United States Patent [19]

Stokbroekx et al.

[11] Patent Number: 5,530,011
[45] Date of Patent: Jun. 25, 1996

[54] 4-[(2-BENZOTHIAZOLYL)METHYLAMINO]-α-[(3,4-DIFLUOROPHENOXY)METHYL]-1-PIPERIDINEETHANOL

[75] Inventors: Raymond A. Stokbroekx, Beerse; Gilbert A. J. Grauwels, Kessel-Lo, both of Belgium

[73] Assignee: Janssen Pharmaceutica N.V., Beerse, Belgium

[21] Appl. No.: 410,168

[22] Filed: Mar. 24, 1995

Related U.S. Application Data

[62] Division of Ser. No. 98,297, filed as PCT/EP92/00356, Feb. 14, 1992, Pat. No. 5,434,168.

[30] Foreign Application Priority Data

Feb. 14, 1992 [WO] WIPO .............. PCT/EP92/00356

[51] Int. Cl.$^6$ .................... A61K 31/445; C07D 417/12
[52] U.S. Cl. ............................. 514/321; 546/198
[58] Field of Search ............... 514/321; 546/198

[56] References Cited

U.S. PATENT DOCUMENTS 4,861,785  8/1989  Stokbroekx et al. ............. 514/321

OTHER PUBLICATIONS

Van Reempts et al. "Structural cell damage and reginal blood flow in the hypoxic brain ..." Proceedings Inte. Symposium on Pharm. Cerebral Ischemia, (1986) pp. 385–390.

*Primary Examiner*—Ceila Chang
*Attorney, Agent, or Firm*—Charles J. Metz

[57] ABSTRACT

A compound of formula

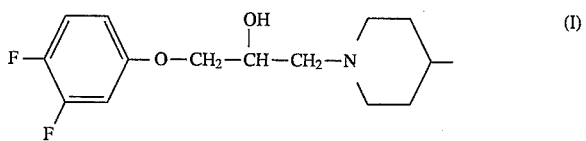

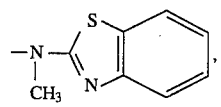

the racemic mixture, the (S)-form and the acid addition salts thereof, said compound having anti-stroke properties. Pharmaceutical compositions containing this compound as active ingredient and a method of preparing said compound and pharmaceutical compositions.

4 Claims, No Drawings

4-[(2-BENZOTHIAZOLYL)METHYLAMINO]-α-[(3,4-DIFLUOROPHENOXY)METHYL]-1-PIPERIDINEETHANOL

CROSS-REFERENCE TO RELATED APPLICATIONS

This application is a divisional of application Ser. No. 08/098,297, filed Aug. 3, 1993, now U.S. Pat. No. 5,434,168, which was based upon PCT Application No. PCT/EP 92/00356, filed Feb. 14, 1992.

BACKGROUND OF THE INVENTION

In U.S. Pat. No. 4,861,785 there are described benzoxazol- and benzothiazolamine derivatives having anti-anoxic activity. The benzothiazole compounds of the present invention show unexpected anti-stroke activity when compared to the structurally related compound sabeluzole.

DESCRIPTION OF THE INVENTION

The present invention is concerned with the racemic mixture and the (S)-form of 4-[(2-benzothiazolyl)methylamino[-α-[(3,4-difluorophenoxy)methyl]- 1-piperidineethanol which may be represented by the formula

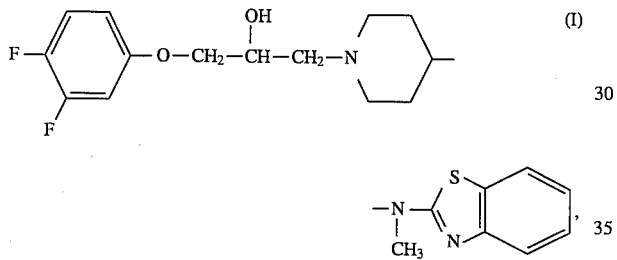

and the pharmaceutically acceptable acid addition salts thereof.

The acid addition salts as mentioned hereinabove are meant to comprise the therapeutically active non-toxic acid addition salt forms which the compound of formula (I) is able to form. The latter can conveniently be obtained by treating the base form with appropriate acids, such as, for example, inorganic acids, such as hydrohalic acid, e.g. hydrochloric, hydrobromic acid and the like, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic, 7,7-dimethyl-2-oxobicyclo[2,2,1]heptane-1-methanesulfonic, 2-[(4-methylphenyl)sulfonylamino]pentanedioic and the like acids. Conversely the salt form can be converted into the free base form by treatment with alkali.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

The compounds of this invention have an asymmetric carbon atom and the absolute configuration of this asymmetric centre may be indicated by the stereochemical descriptors R and S. Unless otherwise mentioned or indicated, the chemical designation of compounds denotes the mixture of all possible stereochemically isomeric forms.

Hereinafter the term 'enantiomerically pure' concerns compounds having an enantiomeric excess of at least 94% (i.e. minimum 97% of one enantiomer and maximum 3% of the other enantiomer) up to an enantiomeric excess of 100% (i.e. 100% of one enantiomer and none of the other), in particular compounds having an enantiomeric excess of 96% up to 100%, more in particular having an enantiomeric excess of 98% up to 100%.

Preferred compounds within the invention are:
(S)-4-[(2-benzothiazolyl)methylamino]-α-[(3,4-difluorophenoxy)methyl]-1-piperidine ethanol and its dihydrochloride salt.

The compounds of formula (I) can generally be prepared by N-alkylating a piperidine of formula (II) with an alkylating reagent of formula (III) following art-known N-alkylation procedures.

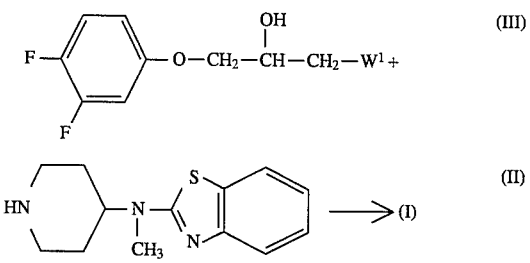

In formula (III) $W^1$ represents an appropriate reactive leaving group such as, for example, halo, e.g. chloro, bromo or iodo; sulfonyloxy, e.g. methanesulfonyloxy, trifluoromethanesulfonyloxy, benzenesulfonyloxy, 4-methylbenzenesulfonyloxy and the like leaving groups. Said N-alkylation reaction can conveniently be carried out by mixing the reactants, optionally in a reaction-inert solvent such as, for example, an aromatic solvent, e.g. benzene, methylbenzene, dimethylbenzene and the like; a $C_{1-6}$alkanol, e.g. methanol, ethanol, 1-butanol and the like; a ketone, e.g. 2-propanone, 4-methyl- 2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent. e.g. N,N-dimethylformamide, N,N-dimethylacetamide, dimethylsulfoxide, pyridine, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary, amine, e.g. N,N-diethylethanamine, N-(1-methylethyl)-2-propanamine, 4-ethylmorpholine, 1,4-diazabicyclo[2.2.2] octane, pyridine and the like, may optionally be used to pick up the acid which is formed during the course of the reaction. In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Alternatively, said N-alkylation may be carried out by applying art-known conditions of phase transfer catalysis reactions. Somewhat elevated temperatures may be appropriate to enhance the rate of the reaction.

In this and the following preparations, the reaction products may be isolated from the medium and, if necessary, further purified according to methodologies generally known in the art such as, for example, extraction, crystallization, trituration and chromatography.

The compound of formula (I) can also be obtained by reacting a piperidine of formula (II) with an epoxide of formula (IV).

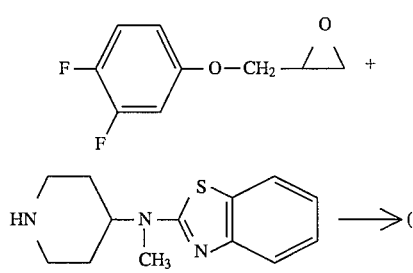

This reaction may be conducted by stirring and, if desired, heating the reactants in a reaction-inert solvent such as, for example, water, an aromatic hydrocarbon, e.g. benzene, methylbenzene and the like; an alcohol, e.g. methanol, ethanol, isopropanol, 1-butanol and the like; a ketone, e.g. 2-propanone, 4-methyl-2-pentanone and the like; a dipolar aprotic solvent, e.g. N,N-dimethylformamide, N,N-dimethylacetamide and the like; or a mixture of such solvents.

The compounds of formula (I) may also be prepared by cyclizing a thiourea derivative of formula (VII), which may be formed by reacting an amine of formula (V) with an isothiocyanate of formula (VI) in a suitable reaction-inert solvent, such as, for example, an alkanol, an ether, a ketone or the like.

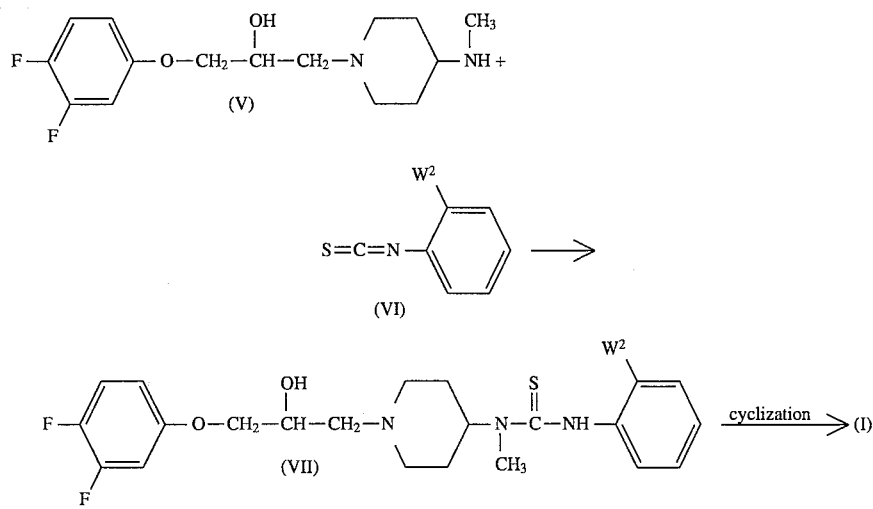

In formula (VI) and (VII) $W^2$ represents for example, hydrogen, halo, e.g. chloro and bromo; $C_{1-6}$alkyloxy or $C_{1-6}$alkylthio. Said cyclization reaction may optionally be carried out in the presence of an appropriate oxidant such as, for example, a dihalide, e.g. chlorine or bromine. Said cyclization reaction can be carried out in a reaction-inert solvent such as, for example, a halogenated hydrocarbon, e.g. tetrachloromethane, trichloromethane, dichloromethane and the like; a hydrocarbon, e.g. benzene, methylbenzene, hexane and the like; an ether, e.g. tetrahydrofuran and the like; a ketone, e.g. 2-propanone, 2-butanone and the like; an alcohol, e.g. methanol, ethanol, 2-propanol and the like; a dipolar aprotic solvent, e.g. N,N-dimethylformamide, N,N-dimethylacetamide and the like. Elevated temperatures and stirring may enhance the reaction rate.

The compound of formula (I) may alternatively be prepared by reacting an appropriate reagent of formula (VIII) with a benzothiazole of formula (IX).

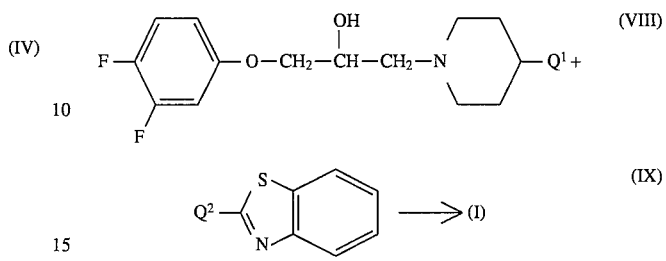

In (VIII) and (IX) $Q^1$ and $Q^2$ are selected so that during the alkylation reaction a radical of formula —N(CH$_3$)— is formed. For example, where $Q^1$ is an appropriate leaving group, $Q^2$ is a radical of formula —NH(CH3), or where $Q^1$ is a radical of formula —NH(CH3), $Q^2$ is an appropriate leaving group. An appropriate leaving group is, for example, a halo, eg. chloro, bromo and the like; a sulfonyloxy group, e.g. methanesulfonyloxy, 4-methylbenzenesulfonyloxy and the like. The reaction can be carried out in a reaction-inert solvent such as, for example, an aromatic hydrocarbon, e.g. benzene, methylbenzene and the like; an ether, e.g. 1,4-dioxane, tetrahydrofuran and the like; a halogenated hydrocarbon, e.g. trichloromethane, tetrachloromethane and the like; an alkanol, e.g. methanol, ethanol, 1-butanol and the like; a ketone, e.g. 2-propanone, 4-methyl-2-pentanone and the like: a dipolar aprotic solvent, e.g. N,N-dimethylformamide, N,N-dimethylacetamide and the like. The addition of an appropriate base, such as, for example, an alkali metal carbonate or hydrogen carbonate, e.g sodium carbonate, sodium hydrogen carbonate and the like; sodium hydride; or an organic base, such as, for example, N,N-diethylethanamine and the like may be used to pick up the acid which is formed during the course of the reaction.

The compounds of formula (I) may also be prepared by reacting a N-substituted 4-piperidinone of formula (X) with a benzothiazolamine of formula (XI) following art-known reductive N-alkylation procedures.

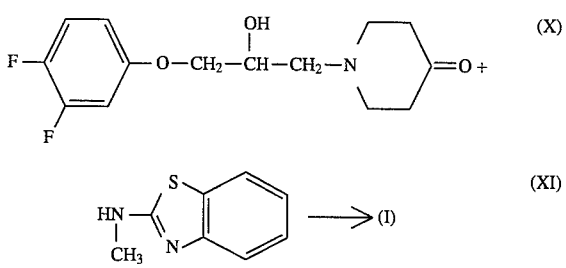

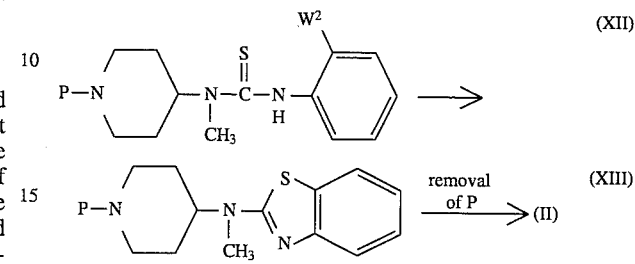

The reaction of (X) with (XI) can conveniently be carried out by mixing the reactants in a suitable reaction-inert solvent with an appropriate reductant. Preferably, the ketone of formula (X) is first reacted with the intermediate of formula (XI) to form an enamine, which optionally may be isolated and further purified, and subsequently reducing said enamine. Suitable solvents are, for example, water, $C_{1-6}$alkanols, e.g., methanol, ethanol, 2-propanol and the like; ethers. e.g., 1,4-dioxane and the like; halogenated hydrocarbons, e.g., trichloromethane and the like; dipolar aprotic solvents, e.g., N,N-dimethylformamide, N,N-dimethylacetamide, dimethylsulfoxide and the like; or a mixture of such solvents. Appropriate reductants are for example, metal or complex metal hydrides, e.g., sodium borohydride, sodium cyanoborohydride, lithium aluminum hydride and the like. Alternatively, hydrogen in the presence of a suitable catalyst such as, for example, palladium-on-charcoal, platinum-on-charcoal and the like may be used as reductant. In order to prevent the undesired further hydrogenation of certain functional groups in the reactants and the reaction products it may be advantageous to add an appropriate catalyst poison to the reaction mixture such as, for example, thiophene and the like.

Enantiomerically pure forms of the compounds of formula (I) can be obtained by converting a racemic mixture of the compounds of formula (I) with a suitable resolving reagent such as, for example, a chiral acid, e.g. tartaric, malic and mandelic acids, camphor sulfonic acid, 4,5-dihydro-1H-2-benzopyran-2-carboxylic acid and the like to a mixture of diastereomeric salts; physically separated said mixtures by, for example, selective crystallization or chromatographic techniques, e.g. liquid chromatography and the like methods; and finally converting said separated diastereomeric salts into the corresponding enantiomeric forms of the compound of formula (I) by hydrolysis in an acidic or basic aqueous medium, optionally at an elevated temperature.

Alternatively, enantiomerically pure forms can conveniently be obtained from the enantiomerically pure isomeric forms of the appropriate starting materials, provided that the subsequent reactions occur stereospecifically. For example, the enantiomerically pure forms of compound (I) can be prepared by reacting an enantiomerically pure epoxide of formula (IV) with an intermediate of formula (II), as described hereinabove. The enantiomerically pure epoxide of formula (IV) can be prepared by reacting 3,4-difluorophenol with an enantiomerically pure epoxide of formula (XVII), as described hereinafter.

As a further alternative, the enantiomers may be separated by liquid chromatography using a chiral stationary phase.

A number of intermediates and starting materials in the foregoing preparations are known compounds which may be prepared according to art-known methodologies of preparing said or similar compounds. The procedures for preparing some other intermediates will be described hereinafter in more detail.

The intermediate of formula (II) can be prepared by oxidatively cyclizing a thiourea derivative of formula (XII), wherein P is an appropriate leaving group such as, for example, $C_{1-6}$alkyloxycarbonyl, phenylmethoxycarbonyl, phenylmethyl and the like, and $W^2$ is as defined hereinabove following the same procedures as described hereinbefore for the preparation of (I) starting from (VII) and, subsequently removing the protective group P in the thus obtained intermediate (XIII).

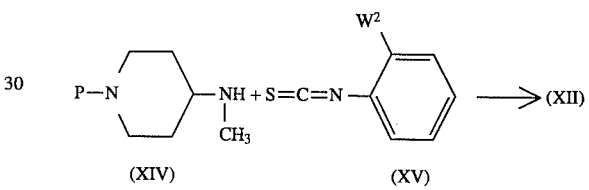

The removal of the protective group P in (XIII) may be carried out following art-known procedures such as, for example, by hydrolysis in an acidic or alkaline aqueous medium or by catalytic hydrogenation, depending upon the nature of P.

Said intermediates of formula (XII) can in turn be prepared by reacting an amine of formula (XIV) with an isothiocyanate of formula (XV) as described hereinbefore for the preparation of (VII) from (V) and (VI).

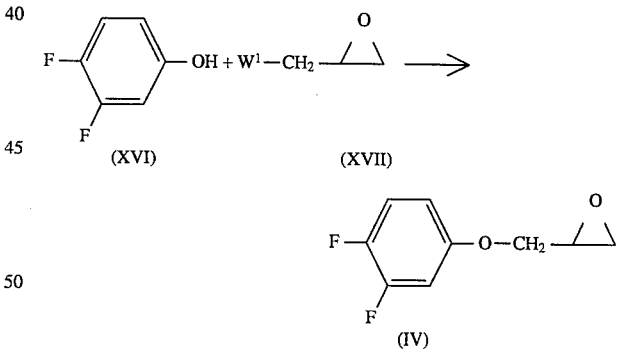

The intermediate of formula (IV) can be prepared by reacting 3,4-difluorophenol (XVI) with an epoxide of formula (XVII). In formula (XVII) $W^1$ has the previously described meaning.

Said alkylation reaction can be carried out as described hereinbefore for the preparation of (I) from (Ill and (III).

The compound of formula (I) (the racemic mixture and the (S)-form) and the pharmaceutically acceptable acid addition salts thereof possess useful in vivo anti-stroke properties, which activity can be evidenced by the test named "Post-Treatment in a Rat Photochemical Stroke Model" which is described in the experimental part hereafter.

The present compounds, like the prior-art compounds from U.S. Pat. No. 4,861,785 (such as sabeluzole) are potent anti-hypoxic agents. An unexpected property of the present compounds over said art compounds resides in the fact that the present compounds are potent in vivo anti-stroke agents, whereas in vivo anti-stroke activity is not observed with the prior art compounds. The anti-stroke activity displayed by the subject compounds is unexpected in view of the fact that the subject compounds are slightly less potent anti-hypoxic agents compared to sabeluzole. Apparently, there is no simple correlation between in vivo anti-hypoxic activity and in vivo anti-stroke activity. Consequently, the subject compounds may be useful in the acute treatment of stroke, whereas the prior-art compounds are only useful in the chronic treatment of stroke, e.g. in maintenance therapy. Further advantages of the subject compounds over the prior-art compounds are the longer duration of anti-hypoxic activity, the absence of sedation and ataxia phenomena in mice and the absence of palpebral ptosis in rats.

In view of their useful pharmacological properties, the subject compounds may be formulated into various pharmaceutical forms for administration purposes. To prepare the pharmaceutical compositions of this invention, an effective amount of the particular compound, in acid addition salt or base tom, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may also be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

Interesting compositions among the groups of compositions are those comprising a cyclodextrin (CD) or an ether derivative thereof, as a complexant and/or solubilizer. As examples of such cyclodextrins there may be mentioned $\alpha$-CD, $\beta$-CD, $\gamma$-CD, and ether or mixed ether derivatives thereof.

Particular such cylcodextrin derivatives are described in U.S. Pat. No. 3,459,731, EP-A- 0,149,197 and EP-A-0,197, 571.

Typically such ether or mixed ether derivatives comprise $\alpha$-, $\beta$- or $\gamma$-CD wherein one or more hydroxylgroups are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl. Especially noteworthy as complexants and/or solubilizers are $\beta$-CD, 2,6-dimethyl-$\beta$-CD and in particular 2-hydroxypropyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl-$\beta$ -CD.

In the aforementioned cyclodextrin derivatives, the DS (degree of substitution, i.e. the average number of substituted hydroxy functions per glucose unit) preferably is in the range of 0.125 to 3, in particular 0.2 to 2, or 0.2 to 1.5. More preferably the DS ranges from about 0.2 to about 0.7, in particular from about 0.35 to about 0.5 and most particularly is about 0.4. The MS (molar degree of substitution, i.e. the average number of moles of the substituting agent per glucose unit) is in the range of 0.125 to 10, in particular of 0.3 to 3, or 0.3 to 1.5. More preferably the MS ranges from about 0.3 to about 0.8, in particular from about 0.35 to about 0.5 and most particularly is about 0.4. Said compositions can conveniently be prepared by dissolving the cyclodextrin or ether derivative thereof in water and adding thereto the compound of formula (I) as well as other adjuvants and components such as, for example, sodium chloride, potassium nitrate, glucose, mannitol, sorbitol, xylitol and buffers such as, for example, phosphate, acetate or citrate buffers; and optionally concentrating or drying the solution by evaporation under reduced pressure or by lyophilization; and further optionally reconstituting the lyophilized residue with water. The amount of the cyclodextrin or ether derivative thereof in the final composition generally ranges from about 1% to about 40%, particularly form 2.5% to 25% and more particularly from 5% to 20%.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the anti-stroke properties, the compound of formula (I) (the racemic mixture and the (S)-form) and the acid addition salts thereof, can be used in the acute treatment of subjects suffering from conditions, such as, for example ischaemic stroke, hemorrhagic stroke, subarachnoidal hemorrhage or they can be used in the acute treatment of postasphyxial brain damage in newborns. In a further aspect, the present invention provides a method of treating subjects suffering from said conditions, said method comprising the systemic administration of an effective stroke protective amount of a compound of formula (I) or a pharmaceutically acceptable addition salt thereof. Those of skill in the treatment of such diseases could easily determine the effective amount from the test results presented hereinafter. In general it is contemplated that an effective stroke protective amount would be from about 0.1 mg to about 100 mg per day, more preferably from about 1 mg to about 50 mg per day. It may be appropriate to administer the required dose as two, three, four or more sub-doses at appropriate intervals throughout the day. Said sub-doses may be formulated as unit dosage forms, for example, containing 0.1 to 100 mg, and in particular 1 to 50 mg of active ingredient per unit dosage form.

The compound of formula (I) preferably is administered intravenously. Compositions for intravenous administration may comprise, apart from an effective anti-stroke amount of a compound of formula (I), a buffer system, an isotonizing agent, water, a cyclodextrin or an ether derivative thereof and optionally a further pharmaceutically acceptable ingredient.

The following examples are intended to illustrate and not to limit the scope of the present invention.

EXPERIMENTAL PART

A. Preparation of the Intermediates

Example 1

To a stirred and cooled (ice-bath) mixture of 13.0 g of 3,4-difluorophenol and 200 ml of N,N-dimethylformamide, there were added 4.8 g of a dispersion of sodium hydride in mineral oil (50%) and, after stirring for 1 hour, a solution of 22.8 g of (S)-(oxiranylmethyl) 4-methylbenzenesulfonate (ester) in some N,N-dimethylformamide. Stirring at room temperature was continued overnight. The reaction mixture was poured into ice-water and the product was extracted with methylbenzene. The extract was washed with NaCl (dil.) and water and was then dried, filtered and evaporated. The residue was distilled (13.3 Pa, 55° C.), yielding 9.5 g (51.0%) of (S)-[(3,4-difluorophenoxy)methyl]oxirane (interm. 1).

Example 2

A mixture of 117.1 g of 3,4-difluorophenol, 185.5 g of chloromethyloxirane, 125 g of potassium carbonate and 500 ml of 2-propanone was stirred for 48 hours at reflux temperature. The reaction mixture was evaporated and the residue was taken up in dichloromethane. The whole was washed successively with water, NaOH (aq.) (2×) and water, and was then dried, filtered and evaporated. The residue was distilled (13.3 Pa, 58° C.), yielding 90.4 g (54.0%) of [(3,4-difluorophenoxy)methyl]oxirane (interm. 2).

B. PREPARATION OF THE FINAL COMPOUNDS

Example 3

A mixture of 3.4 g of intermediate 2, 6.1 g of N-methyl-N-(4-piperidinyl)-2-benzothiazolamine dihydrobromide, 100 ml of 2-propanol and 5.3 g of sodium carbonate was stirred overnight at reflux temperature. The reaction mixture was evaporated and the residue was partitioned between water and dichloromethane. The organic layer was separated, dried, filtered and evaporated. The residue was purified by column chromatography (silica gel; CHCl₃/CH₃OH 98:2). The eluent of the desired fraction was evaporated and the residue was convened into the dihydrochloride salt in 2-propanol. The product was filtered off, washed with 2-propanol and 2,2'-oxybispropane and dried at 60° C. and at 80° C., yielding 6.1 g (80.3%) of 4-(2-benzothiazolymethylamino)-α -[(3,4-difluorophenoxy)methyl]-1-piperidineethanol dihydrochloride; mp. 211.8° (comp. 1).

In a similar manner there was also prepared:

(−)-(S)-4-[(2-benzothiazolyl)methylamino]-α-[(3,4-difluorophenoxy)methyl]-1-piperidineethanol (E)-2-butenedioate(1:1); mp. 167.8° C.; $[\alpha]_D^{20}$=−7.44° (conc.=1% in methanol) (comp. 2).

Example 4

To a stirred mixture of 10 g of intermediate 1; 14.3 parts of N-methyl-N-(4-piperidinyl)- 2-benzothiazolamine (prepared as described in U.S. Pat. No. 4,861,785); 14.2 g of sodium carbonate and 112 ml of 1-butanol there were added dropwise 11.2 ml of water. After stirring for 16 hours at reflux temperature, the reaction mixture was diluted with 100 ml of water. The organic layer was separated, dried, filtered and evaporated. The residual oil was dissolved in 200 ml of dichloromethane and this solution was stirred for 2 hours with 50 g of silica gel. The silica gel was filtered off and washed with a mixture of dichloromethane and methanol (95:5). The filtrate was evaporated and the residual oil was crystallized from 2,2'-oxybispropane. The product was filtered off and dried at 50° C., yielding 7.5 g (38.7%) of (+)-(S)-4-[(2-benzothiazolyl)methylamino]-α-[( 3,4-difluorophenoxy)methyl]-1-piperidineethanol: mp. 65.8° C.; $[\alpha_D^{20}$=+4.38° conc.=1% in methanol) (comp. 3).

In a similar manner there was also prepared: (+)-(RS)-4-[(2-benzothiazolyl)methyl-amino]-α-[(3,4-difluorophenoxy)methyl]-1-piperidineethanol; mp. 86.4° C. (comp. 4).

Example 5

4.0 g of compound 2 were treated with ammonia to obtain the free base. The solution was evaporated and the residue was converted into the dihydrochloride salt in 2-propanol. The salt was filtered off, washed with 2-propanol and 2,2'-oxybispropane and dried in vacuo at 30° C., yielding 3.0 g (81.4%) of (−)-(S)-4-[(2-benzothiazolyl)methylamino] -α-[(3,4-difluorophenoxy)methyl]-1-piperidineethanol dihydrochloride; mp. 148.7° C.: $[\alpha]_D^{20}$= −9.01° (conc.=1% in methanol) (comp. 5).

Example 6

To a stirred solution of 6.9 g of compound 3 in 100 ml of 2-propanone were added dropwise 10 ml or 2-propanol saturated with hydrogen bromide at room temperature. The precipitate was filtered off and the filtrate was evaporated. The residue was converted into the hydrobromide salt in 2-propanone. The product was filtered off, washed with 2,2'-oxybispropane and dried at 60° C., yielding 5.5 g (58.1%) of (−)-(S)-4-[(2-benzothiazolyl)methylamino]-α-[(3,4-difluorophenoxy)methyl]-1-piperidineethanol dihydrobromide; mp. 213.7° C. (comp. 6).

Example 7

To a stirred solution of 4.38 g of compound 3 in 150 ml of ethyl acetate were added 9.40 g of 7,7-dimethyl-2-oxobicyclo[2.2.1]heptane-1-methanesulfonic acid. The reaction mixture was heated until it became homogeneous. After cooling to 20° C., the whole was stirred for 24 hours. The crystallized product was filtered off, washed twice with 25 ml of ethyl acetate and dried in vacuo at 50° C., yielding 7 g (77.9%) of (+)-(S)-4-[(2-benzothiazolyl)methylamino]-α-[(3,4-difluorophenoxy)methyl]-1-piperidineethanol (S)-7,7-dimethyl-2-oxobicyclo[2.2.1]heptane-1-methanesulfonate (1:2); mp. 119.5° C. (comp. 7).

Example 8

To a stirred solution of 4.38 g of compound 3 in 100 ml of 2-propanol were added 3.11 g of (+)-(L)-2-[(4-methylphenyl)sulfonylamino]pentanedioic acid. The reaction mixture was heated until it became homogeneous. After cooling slowly to 20° C., the reaction mixture was stirred for 68 hours at 20° C. The precipitated product was filtered off, washed with 25 ml of 2-propanol and dried in vacuo at 50° C., yielding 6.87 g (93.5%) of (+)-(S)-4-[(2-benzothiazolyl)methylamino]-α-[(3,4-difluorophenoxy)methyl]-1-piperidineethanol (+)-(L)-2-[(4-methylphenyl)sulfonyl]amino] pentanedioate (1:1) (comp. 8).

PHARMACOLOGICAL EXAMPLES

The useful anti-stroke properties of the compounds of formula (I) are demonstrated in the following test procedure.

Example 9

Post-Treatment in a Rat Photochemical Stroke Model

Male Wistar rats, weighing 260–280 g, were anesthetized with halothane in a $N_2O/O_2$ mixture. Animals were placed in a stereotactic apparatus, the scalp was incised for exposure of the skull surface, and a catheter inserted into a lateral tail vein. Rose Bengal (30 mg/kg; 15 mg/ml in 0.9% NaCl) was infused intravenously for 2 minutes in animals with normal hemodynamics and blood gases. Thereafter, the skull was focally illuminated with cold white light for 5 minutes by means of a fiber-optic bundle inside a 1-mm diameter objective. The light was aimed at the hindlimb area of the right parietal sensorimotor neocortex. Five minutes after infarct induction (i.e. 5 min after light offset) rats were injected with a single intravenous (iv) bolus of compound 5 or its vehicle, 10% hydroxypropyl-β-cyclodextrine.

Neurologic tests, involving limb placing reactions, were conducted on the first two days after infarction at 24-hour intervals after its induction. Tactile forward and sideways placing were tested by lightly contacting the table edge with the dorsal or lateral aspect of a paw (2 tests). Proprioceptive forward and sideways placing involved pushing the paw against the table edge in order to stimulate limb muscles and joints (2 tests). Rats were also put along the edge of an elevated platform in order to assess proprioceptive adduction a paw was gently pulled down and away from the platform edge, and, upon sudden release, it was checked for retrieval and placing (1 test). For each of the 5 tests placing scores were: (0), no placing; 1, incomplete and/or delayed placing; or 2, immediate, complete placing. For each limb, the summed tactile/proprioceptive placing score, including the platform test, was maximally 10. We report results from the deficient hindlimb contralateral to the neocortical infarct. Six rats were used for each dose. The test-results for compound 5 are given below.

Table 1 lists median and extreme limb placing scores along with the number of rats protected (score≧5) on post-infarct days 1 and 2. The $ED_{50}$ for compound 5, that is the dose that produced protection of neurologic function in 50% of the rats, and its 95% confidence limits, was 0.16 (0.13–0.20) and 0.13 (0.08–0.20) mg/kg iv on post-infarct days 1 and 2, respectively.

TABLE 1

| iv Dose of Compound 5 | Neurologic Score (max. = 10) | | Rats Protected |
|---|---|---|---|
| (mg/kg) | Median | Extremes | (out of 6) |
| Post Infarct Day 1 | | | |
| 0.00 | 1 | 0–3 | 0 |
| 0.08 | 3 | 0–4 | 0 |
| 0.16 | 4.5 | 3–9 | 3 |
| 0.31 | 7.5 | 6–10 | 6 |
| 0.63 | 9 | 7–10 | 6 |
| 1.25 | 9 | 7–10 | 6 |
| 2.50 | 9 | 8–10 | 6 |
| Post Infarct Day 2 | | | |
| 0.00 | 1 | 0–3 | 0 |
| 0.08 | 4 | 0–6 | 1 |
| 0.16 | 7 | 2–10 | 4 |
| 0.31 | 10 | 7–10 | 6 |
| 0.63 | 9.5 | 8–10 | 6 |
| 1.25 | 10 | 8–10 | 6 |
| 2.50 | 10 | 9–10 | 6 |

Example 10

Post-Treatment in a Rat Photochemical Stroke Model

Test conditions are equal to those described in Example 9, except that 60 minutes after injection of the intravenous bolus an invariant oral dose of 10 mg/kg of the test compound was supplied to the test animals.

The test results for a number of the present compounds are compared with those from two reference compounds, disclosed in U.S. Pat. No. 4,861,785.

Table 2 lists median and extreme limb placing scores along with the number of rats protected (score≧5) on post-infart day 2, after administering a dose of 1.25 mg/kg iv+10 mg/kg p.o. of the test compound.

TABLE 2

| | Post Infarct Day 2 | | | |
|---|---|---|---|---|
| | Neurologic Score (max = 10) | | | Rats Protected |
| Compound no. | Median | Min. | Max | (out of 6) |
| 5 | 8 | 7 | 10 | 6 |
| 2 | 10 | 8 | 10 | 6 |
| 1 | 10 | 7 | 10 | 6 |
| 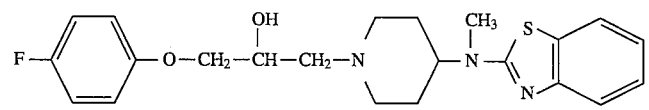 | 0 | 0 | 1 | 0 |

TABLE 2-continued

| | Post Infarct Day 2 | | | |
| --- | --- | --- | --- | --- |
| | Neurologic Score (max = 10) | | | Rats Protected |
| Compound no. | Median | Min. | Max | (out of 6) |
| Cl—[phenyl(Cl)]—O—CH₂—CH(OH)—CH₂—N—[piperidine(CH₃)]—N—[benzothiazole] | 0 | 0 | 8 | 2 |

C. COMPOSITION EXAMPLES

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

Example 11

Injectable Solutions a) 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 1 g of the A.I. The solution is cooled to room temperature and supplemented with water for injection q.s. ad 1 l volume, giving a solution of 1 mg A.I. per ml. The solution is sterilized by filtration (U.S.P. XVII p. 811) and filled in sterile containers.

| b) Active Ingredient | 4 mg |
| --- | --- |
| Sodium chloride | 3.59 mg |
| Sodium citrate 2 aq | 5.8 mg |
| Citric acid 1 aq | 62 µg |
| Hydroxypropyl-β-cyclodextrin (MS = 0.4) | 100 mg |
| Hydrochloric acid (1N) or Sodium hydroxide (1N) | q.s. ad pH 6.9 |
| Water | q.s. ad 1 ml |

Method of Preparation 18 l cold pyrogen free water is sterilized by filtration. Thereto are added with stirring 2 kg hydroxypropyl-α-cyclodextrin (M.S.=0.4), 116 g sodium citrate.2aq, 1.24 g citric acid.1 aq and 71.8 g sodium chloride. The solution is cooled to 25° C. and the pH is adjusted to pH 6.9 by addition of NaOH (1N) or HCl (1N). The solution is stirred until homogenous and cooled at 2° C. to 8° C. 80 g of a compound of formula (I) is added to the citric acid buffer solution and stirred for 5 minutes at a temperature below 8° C. This solution is diluted with cold pyrogen free water to a final volume of 20 l and is sterilized by filtration under sterile nitrogen. The final solution is filled into sterile 1 ml containers.

The following formulation is prepared similarly employing suitable amounts of the ingredients in order to obtain a final solution of the required composition.

| c) Active Ingredient | 1 mg |
| --- | --- |
| Hydrochloric acid (1N) | 6.35 mg |
| Hydroxypropyl-β-cyclodextrin | 10 mg |
| Glucose, anhydrous | 46 mg |
| Sodium hydroxide (1N) | q.s. ad pH 4 |
| Water | q.s. ad 1 ml |

Example 12

Oral Drops 50 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 1 mg/ml of the A.I. The resulting solution is filled into suitable containers.

Example 13

Oral Solution 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 8 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry, and 2 ml of gooseberry essence are added. The latter solution is combined with the former, water is added q.s. to a volume of 20 l providing an oral solution comprising 2 mg of the A.I. per teaspoonful (5 ml). The resulting solution is filled in suitable containers.

Example 14

Capsules 2 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 2 mg of the A.I.

Example 15

Film-coated Tablets

Preparation of Tablet Core

A mixture of 10 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex®). The whole is mixed well and compressed into tablets, giving 10,000 tablets, each comprising 1 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

We claim:

1. A method of treating strokes in patients suffering from the same which comprises administering to said patients an effective anti-stroke amount of a compound of the formula:

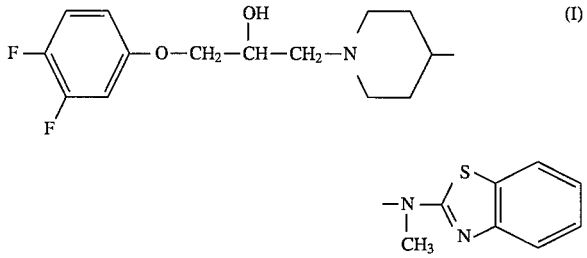

the racemic mixture, the (S)-form, or a pharmaceutically acceptable acid addition salt thereof.

2. The method of claim 1 wherein the compound of Formula (I) is selected from the group consisting of (S)-4-[(2-benzothiazolyl)methylamino]-α-[(3,4-difluorophenoxy)methyl]-1-piperidineethanol and its dihydrochloride salt.

3. A method of treating warm-blooded newborn patients suffering from postasphyxial brain damage which comprises administering to said patients an effective amount of a compound of the formula:

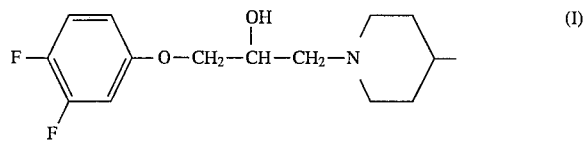

the racemic mixture, the (S)-form, or a pharmaceutically acceptable acid addition salt thereof.

4. The method of claim 3 wherein the compound of Formula (I) is selected from the group consisting of (S)-4-[(2-benzothiazolyl)methylamino]-α-[(3,4-difluorophenoxy)methyl]-1-piperidineethanol and its dihydrochloride salt.

* * * * *